US006090389A

United States Patent [19]

Chen

[11] Patent Number: 6,090,389
[45] Date of Patent: *Jul. 18, 2000

[54] METHOD AND PREPARATIONS FOR THE TREATMENT OF FUNGUS

[76] Inventor: Yu Chen, 1520 Taylor Ave., Baltimore, Md. 21234

[ * ] Notice: This patent is subject to a terminal disclaimer.

[21] Appl. No.: 09/177,973

[22] Filed: Oct. 26, 1998

Related U.S. Application Data

[63] Continuation of application No. 08/748,949, Nov. 14, 1996, Pat. No. 5,837,254.
[51] Int. Cl.⁷ .............................. A61K 35/78; A61K 9/20; A61K 9/48
[52] U.S. Cl. ...................... 424/195.1; 424/430; 424/456; 424/464; 514/937; 514/945; 514/962; 514/967
[58] Field of Search ................................. 424/195.1, 451, 424/452, 465, 430, 433, 464, 422, 456; 514/944, 967, 945, 962, 937

[56] References Cited

U.S. PATENT DOCUMENTS 5,837,254   11/1998   Chen .................................... 424/195.1

OTHER PUBLICATIONS

Bensky et al. Chinese Herbal Medicine, Materia Medica, pp. 81 and 82, 1990.
Tan et al. Phytochemistry, 41:111–116, 1996.
The Merck Manual, vol. 1, General Medicine, 15th Edition, Merck & Co., Inc., Rahway, NJ, pp. 106, 207, 188, 189, and 1372–1374, 1987.
Shih–Chen, Chines Medicinal Herbs, pp. 186–187, 1973.
The Merck Index, 12th Edition, Merck & Co., Inc., Whitehouse Station, NJ, p. 745, Entry #4399, 1996.

*Primary Examiner*—Michael G. Wityshyn
*Assistant Examiner*—Janet M. Kerr
*Attorney, Agent, or Firm*—Sam Silverberg

[57] ABSTRACT

A method and preparations for the treatment of vaginal yeast and other yeast infections is provided for the treatment of infections caused by *Candida albicans* and *Cryptococcus neoformans*. The method and preparations of the invention can also be used for other yeast and fungal infections including systemic, mucosal and cutaneous caused by Candida and Cryptococcus. The vaginal antiyeast and antifungal preparations include, in addition to suppositories and mouth washes, troches, lotions, creams, tablets and capsules containing gentian preparations as an active ingredient obtained from the plant *Radix gentianae* Longdancao. For systemic fungal infections gentian preparations from the plant *Radix gentianae* Longdancao are taken orally in the form of lozenges, tablets, capsules or in solution form for gargling or swallowing.

21 Claims, No Drawings

METHOD AND PREPARATIONS FOR THE TREATMENT OF FUNGUS

This application is a continuation of U.S. Application Ser. No. 08/748,949 filed Nov. 14, 1996 now U.S. Pat. No. 5,837,254.

BACKGROUND OF THE INVENTION

1. Field of the Invention

The present invention pertains to a method and novel compositions containing gentian from the gentianaceae family of plants for the treatment of vaginal yeast infections and other fungal infections caused by various fungal and yeast forms such as Candida and Cryptoccus. More particularly, the invention pertains to novel compositions and preparations obtained from the root or seeds of the plant having the pharmaceutical name of *Radix gentianae* Longdancao for the treatment of vaginal yeast infections and other fungus and yeast infections caused by *Candida albicans* and Cryptoccus.

The plant *Radix gentianae* Longdancao is also known by the botanical names *Gentiana scabra* Bge, *Gentiana triflora* Pall, *Gentiana manshurica* Kitag, *Gentiana algida* Pall, *Gentiana regescens* Fransh and *Gentiana lutea* which will be referred to collectively as *Radix gentianae* Longdancao. *Radix gentianae* Longdancao may be used to prepare novel antifungal preparations and novel medicaments in the form of topical creams, liquids, lotions, capsules, lozenges and suppositories. The novel preparations from *Radix gentianae* Longdancao may be applied topically or transmucosally to treat cutaneous and mucosal syndromes caused by candida infection or taken internally in the form of lotions, liquids, tablets and capsules for the treatment of systemic Candida and Cryptoccus infections.

The novel method of treatment of Candida and Cryptoccus infection with novel preparations from *Radix gentianae* Longdancao is effective in treating not only cutaneous and mucosal candidiasis but also systemic candidiasis involving the bloodstream and metastatic invasion of the meninges, bones, joints, peritonium and myocardium. The novel *Radix gentianae* Longdancao preparations, when taken internally, pass through the digestive system and enter the blood stream for the treatment of systemic Candida infections and pass the blood brain barrier to treat meningeal candidiasis and Cryptoccus meningitis in AIDS patients. The novel preparations of the invention do not require injection or IV application for the treatment of fungal infections of *Candida albicans*, *Candida tropicalis* and other Candida species referred to collectively as Candida and *Cryptoccus neoformans* and other Cryptoccus species collectively referred to as Cryptoccus. The novel *Radix gentianae* Longdancao preparations are advantageous over the prior art since they are nontoxic to the patient and may be utilized in patients having weak or compromised immune systems such as in the case of AIDS patients, leukemia, Hodgkin's disease, neutropenia, hematologic diseases and endocrinopathies.

The method and novel preparations of the invention may also be utilized to treat the mucus membrane infections such as vaginal yeast infections, oral candidiasis and urinary tract candidiasis in both patients with normal immune systems and immuno-compromised patients through the use of suppositories and solutions prepared from the *Radix gentianae* Longdancao. The novel preparations may be applied in the form of suppositories, liquids, creams and other formulations for use in the treatment of mucosal infestations of *Candida albicans* such as in the case of vaginal yeast infections, oral thrush or oropharyngeal moniliasis and for systemic infections caused by Candida and Cryptoccus by the utilization of capsules, lotions and liquids prepared in accordance with the present invention.

2. Description of Related Prior Art

A number of species of the fungus *Candida albicans* are capable of causing candidiasis. *Candida albicans* can switch reversibly and at high frequency among at least seven different phenotypes defined by colony morphology. The changes in *Candida albicans* are often associated with changes in virulence which are related to the particular balance of the flora composition in the particular organ as well as immunological condition of the patient. Candida and Cryptoccus are ubiquitous in the environment and generally do not create problems, except where the immune system is weak or compromised or the normal floral balance of the skin, mucous membranes, gastrointestinal tract or body is changed as a result of a variety of factors such as stress, changes in pH, nutrition and changes in the immune system of the patient. *Candida albicans* is part of the normal flora of the skin, mucous membranes in the mouth, throat, intestine and genital tract. Normally *Candida fungus* lives in a healthy balance with the other bacteria and yeasts in the body as part of the normal flora. As a result infection is always present and *Candida albicans* is the most common systemic mycosis.

A number of environmental stimuli are known to trigger or to block the growth of candidiasis. *Candida flora* is generally kept in balance by killer toxins produced by other yeast and fungus in the normal flora of the body. Abnormal physiological changes in the epithelium may be involved together with a host of other factors, including genetics, nutrition, stress and other factors that result in infections of various organs of the body, particularly in immunosuppressed individuals or in individuals that have had the normal floral balance changed by the taking of wide spectrum antibiotics such as tetracycline. The taking of such wide spectrum antibiotics has in many cases eliminated beneficial flora which keep *Candida albicans* in check and prevented candidiasis.

In addition to a great number of environmental factors a host of immunological conditions of the patient result in varying degrees of susceptibility to candidiasis and Cryptoccus infections. Cancer patients, organ transplant patients and patients with immunologic disorders, chronic infections, leukemia, acquired immunodeficiency disorder diseases (AIDS), Hodgkin's disease, neutropenia and other hematologic diseases and endocrinopathies including diabetes leave the patient particularly susceptible to fungal infections by *Candida albicans* and Cryptoccus. Such immunologically compromised patients are at a risk of systemic candidiasis, *Cryptococcal meningitis* and other infections resulting from the inability of their immune system to destroy ubiquitous fungus of *Candida albicans* and Cryptoccus which are part of the normal environment.

It is known that *Candida albicans* and *Cryptoccus neoformans* are killed by neutrophils in the normally healthy patient. Where the neutrophils have impaired killing capacity or the patient is neutropenic such as those having leukemia or impaired immunological systems such patients are particularly susceptible to *Candida albicans* and *Cryptoccus neoformans*. As a result intact cell mediated immunity is critical to prevent infection against *Candida albicans* and *Cryptoccus neoformans*. In the case of immunologically suppressed patients opportune *Candida albicans* and Cryptococcal infections are particularly difficult to treat. Treatment of AIDS patients with cryptococcal infection are particularly difficult to treat, particularly where *Cryptococcal meningitis* is involved due to problems in the administration of drugs, particularly amphotericin B which is toxic and which must be administered by IV.

In the case of patients with normal immune systems fungal infections of the mouth produce painful oropharyngeal moniliasis or thrush if wide range antibiotics such as tetracycline have destroyed a normal floral balance which blocks the growth of *Candida albicans*. In this regard it is to be noted that there is a confusion of nomenclature and various names have been applied to Candida organisms such as *Monilia albicans, Saccharomyces albicans, Odium albicans* but usually the *Candida albicans* is the most commonly used and will be referred to herein as Candida or *Candida albicans*. *Candida albicans* grows readily in a moist environment at a pH of more than 5. *Lactobacillus* normally maintains the pH at a range of 4.5 to 5 and as a result *lactobacillus* provides a natural floral balance to candidiasis.

Fungal infections of the vagina or urinary tract are difficult to eradicate and frequently recur but are rarely life-threatening. The normal pH of the genital tract is 4.5 to 5 which is maintained by *lactobacillus*. The absence of *lactobacillus* and a normal pH promotes candidiasis as well as the herpes virus, birth control pills, a weak immune system, genetic factors, stress and a host of other factors which foster the growth of yeast and fungal infections of the genital tract.

The treatment of fungus and yeast infections has a long history which originated from herbs, plants and compositions isolated from vegetation. In fact, amphotericin B was isolated from rotting vegetation on the banks of the Oronico River in Venezuela. Amphotericin B, despite its toxicity and the fact that it was discovered back in 1956, still remains the most effective wide spectrum fungicide in use today. Amphotericin B is a polyene and remains the most efficacious and drug of choice for many deep seated fungal infections caused by Candida and Cryptoccus. Amphotericin B however is toxic and has exhibited a number of adverse side effects. Other polyenes in use include nystatin, candicidin, primaricin and mepatricin. The toxicity and adverse side effects of the polyene drugs have in many cases limited their applicability to external and topical applications. See *Scientific American Medicine* (1980), Vol. 2, p. 11–16, 7–8; *Topley and Wilson's Principles of Bacteriology, Virology And Immunity,* 8th ed. (1990), Vol. 1, p. 144–149; Lederberg (ed.) *Encyclopedia of Microbiology,* (1992) Vol. 1, p. 135; *Zinsser Microbiology,* 20th ed. (1992), p. 337–338, 682–686; 1089, 1136–1139, 1142–1143; *Goodman & Gilman's The Pharmacological Basis of Therapeutics,* 9th ed. (1996), p. 207–208; and *Principles of Pharmacology, Paul L. Munson* (1995) p. 1401–1411.

In addition to polyene compounds various azole derivatives including ketoconazole, fluconazole and itraconazole are used for systemic infections. Other azole derivatives include miconazole, clotrimazole, terconazole and econazole. These azole derivatives possess a broad spectrum of antifungal activity, have low toxicity and consequently the azole compounds are in wide use and are administered orally and systemically for systemic infection and are administered topically for dermatophytosis, vaginal mycoses and for skin and mucocutaneous infections. Ketoconazole, fluconazole and itraconazole are typically used for systemic fungal infections and are administered orally.

In addition to the polyene and azole compounds 5-fluorocytosine is commonly used in combination with amphotericin B for systemic infections caused by *Cryptoccus neoformans* and Candida, particularly in immunocompromised patients. In addition other treatments and older treatments for mucosal candidiasis and smooth skin infections with *Candida albicans* have been used such as Whitfields Ointment which is a mixture of 6% benzoic acid and 3% salicylic acid and gentian violet. *Principles of Pharmacology, Paul L. Munson,* (1995), p. 1410 and *The Merck Index,* 10th Ed. (1981), p. 627. Gentian violet is a chemical compound that is not present in gentian plants or gentian root.

A wide variety of pharmaceutical preparations are available for the treatment of candidiasis and Cryptoccus but each has its limitations in its method of administration and situs of activity. None of the available pharmaceutical preparations are both safe, effective, without side effects and can be administered orally and topically. The pharmaceutical preparations of the invention however, are safe, effective and cure candidiasis and Cryptoccus infection effectively without side effects.

Common side effects of the prior art compound Nystatin used for the treatment of oral thrush include nausea, diarrhea and hypersensitivity. Amphotericin B has many side effects, including renal toxicity, thrombophlebitis, hypokalemia, anemia, chills, fever, headache, nausea and anorexia. 5-Fluorocytosine produces skin rashes, diarrhea, nausea, hematopoietic and hepatic toxicities. The azole compounds including miconazole, ketoconazole, itraconazole and fluconazole all have the propensity of causing nausea, vomiting, headache, rash and sometime liver toxicity. These compounds when used to treat candidiasis and yeast infections of the vagina generally require prolonged treatment and in many cases result in recurrent yeast infections. *Novak's Textbook of Gynecology,* 10th Ed. (1980), p. 262–269. This is particularly the case with individuals having a weak immune system which require suppression therapy which require low dose treatments for long periods of time to control mycotic disease. Such suppression therapy is generally described for patients having weak immune systems or recurrent infection in such suppression therapy has been used in conjunction with ketoconazole, oral mystatin or low dose amphotericin B.

Gentian and gentian root have been in use for over 3,000 years as digestive stimulants and as ingredients in drinks and liquors. *The Healing Herbs,* (1991), p. 183–185; *The Honest Herbal,* 3rd Ed. (1993), p. 145. Traditional Chinese medicine has long used *Radix gentianae* Longdancao for a variety of liver, gallbladder and digestive treatments; *Chinese Medicinal Herbs* (1973), p. 81–82; *Chinese Herbal Medicine,* (1986) p. 104. *A Compilation of Chinese Literature in the 1980's,* p. 255–277 also discusses the use and some of the chemical constituents of the plant *Radix gentianae* Longdancao. None of these references describe or discuss a use for gentian as an antifungal or yeast treatment of Candida or Cryptoccus. *The Chemical Constituents of Oriental Herbs,* (1982), p. 105–106, 256, 644–645, 1131, 1175; *CRC Handbook of Medicinal Herbs,* (1986); *Kudo-Chemical Abstracts,* Vol. 114 (1991) abstract 114:254, 021K; *Song Chemical Abstracts,* Vol. 106 (1987) abstract 106:60602q; and *Sadritdinoy-chemical Abstracts,* Vol. 78 (1973) abstract 79634b discuss general medicinal properties of gentian for treatment of fevers, rheumatism, general disability and ulcers, malaria and herpes as well as the chemical constituents of the plant. These references do not teach or suggest a treatment for yeast or fungal infections caused by Candida and Cryptococcus.

Recently and after the present testing of gentian in vivo for the treatment of Candida and Cryptoccus a paper is

*Phytochemistry,* Vol. 41, No. 1, pp. 111–116 (1996) entitled "*Secoiridoids and Antifunaal Aromatic Acids From Gentiana Alaida*" was published. This report substantiates in vitro activity against *Candida albicans* but does not teach or suggest antifungal or antiyeast activity against Cryptoccus or the treatment or activity against systemic candidiasis. This report furthermore does not teach or suggest the antifungal activity in weak or immuno-suppressed patients or the formulations of the invention that can be administered orally to treat Candida and *Cryptoccus mycoses.* It is further believed this recent paper is not prior art to the present invention which reduced the present invention to practice before the publication of this paper. This paper identified two chemical constituents with antifungal activity. They are methyl anofinic acid and methyl fomannoxin acid.

The prior art preparations in addition have not provided a safe, effective and nontoxic treatment of fungal and yeast infections or have cured the yeast infections within a few days to return the body to an immunological state necessary to ward off future fungal attacks. The prior art preparations have also not performed well in the treatment of patients with weak immune systems and have in some cases required injection and IV administration to treat candidiasis and cryptococcal fungal infections. The preparations of the invention unlike the prior art provide a safe, reliable and effective treatment of candidiasis and Cryptoccus in weak and compromised immune-deficient patients and may be administered topically or orally. The novel preparations and treatment of fungal infections caused by Candida and Cryptoccus include the application of gentian in the form of suppositories, capsules, creams, lotions, lozenges and liquid preparations.

SUMMARY OF THE INVENTION

The present invention pertains to a method and pharmaceutical preparations for the treatment of fungus and fungal infections caused by Candida and Cryptoccus. The novel antifungal preparations of the invention contain gentian as an active ingredient and are obtained from the plant *Radix gentianae* Longdancao. The novel antifungal preparations may be applied topically in the form of lotions, creams or sprays for topical fungal infections or may be applied to mucosal surfaces of the body in the form of suppositories, liquids, creams and lotions. Systemic infections caused by Candida and Cryptoccus can be treated with liquid, tablet and capsule preparations for oral ingestion in which the active gentian ingredient passes through the gastrointestinal tract and is absorbed into the blood stream to treat systemic infections of the body and myocardium. The active gentian ingredient absorbed in the blood stream is also able to penetrate the blood brain barrier and treat fungal infections involving the brain including *Cryptoccus meningitis,* as in AIDS patients.

The pharmaceutical preparations of the invention are all obtained from the plant having the pharmaceutical name of *Radix gentianae* Longdancao which is also known by the botanical names of *Gentiana scabra* Bge, *Gentiana triflora* Pall, *Gentiana manshurica* Kitag, *Gentiana algida* Pall, *Gentiana regescens* Fransh, *Gentiana lutia* and possibly others all of which will be referred to collectively as *Radix gentianae* Longdancao or simply gentian. *Radix gentianae* Longdancao may be formulated with a number of different carriers to make the pharmaceutical preparations in the form of suppositories, lotions, solutions, capsules, tablets, troches and solutions for gargling or swallowing for the treatment of fungus and yeast infections.

Unlike the prior art antifungal preparations the novel gentian preparations are safe, effective, nontoxic and do not have undesirable side effects. The novel gentian preparations of the invention have resulted in effective treatment over a period of days instead of weeks and months. In addition the novel pharmaceutical preparations have been tested in vivo in patients having normal and weak immune systems including patients with human immunodeficiency virus (HIV).

The novel gentian preparations administered in accordance with the invention are effective in vivo which demonstrate the value of the novel antifungal preparations of the invention. In vitro test results generally provide a poor correlation of effectiveness due to a complex relationship between the state of a patient's immune system and the existing flora of the infected site. As is known by those skilled in the art the susceptibility to infection particularly is complex and depends upon many factors including the balance between flora at the infection site, nutrition, heredity, the state of the patient's immune system, other drugs and antibiotics in the body and a host of environmental factors. As is further known by those skilled in the art, small changes in pH, number and type of fungus and bacteria and other complex factors dramatically affect the ability of Candida and Cryptoccus to multiply and change their phenotype into virulent forms. The change in phenotype and interrelationship in the human environment is not present in in vitro studies and as a result such in vitro studies have not provided a good correlation to predict in vivo effectiveness of antifungal agents for the treatment of fungus and yeast infections caused by Candida and Cryptoccus.

The invention provides specific in vivo patient examples demonstrating the effectiveness of the method of treatment and pharmaceutical preparations prepared in accordance with the invention. The methods of treatment for vaginal yeast infection and for candidiasis of the mucosa of the mouth, throat and urinary tract include the application of vaginal suppositories and solutions for gargling or swallowing or lozenges and troches for delivering gentian to the affected area which are repeatedly treated. The novel preparations are made by utilizing gentian root and which is prepared from *Radix gentianae* Longdancao by first washing the gentian root with water to remove dust, dirt and contaminants. The cleaned root is then heated from between 100° F. to 200° F. for ½ to 2 hours with the oven door open to remove moisture and to prepare the gentian root for grinding. The gentian root is ground to a fine powder using a 9092 Taiwan Herbal Grinder and the resulting powder may be used to make a solution for gargling or swallowing by treating 20 grams of powdered gentian root with about 100 ml of water and bringing the mixture to a boil and simmering about 20 minutes. To this solution flavorings, sweeteners, but not sugar, or other excipients or carriers may be added as are commonly known to those skilled in the art.

Troches, lozenges and capsules can be formulated from cleaned and ground gentian root by adding sweeteners other than sugar, flavorings or other excipients or carriers to the gentian root to provide a final product having about at least 10% and preferably at least 20% gentian root as an active ingredient. The resulting mixture can be coated with a gelatin coating or compounded into solid lozenges and troches as are commonly known to those skilled in the art. The troches, lozenges or capsules are then administered orally and dissolved by the patient in the mouth to treat mucosal infection by Candida of the mouth and throat.

The novel gentian pharmaceutical preparations for the treatment of systemic candidiasis and Cryptoccus are administered in the form of liquids, capsules and tablets for adults. The novel gentian formulations may also be administered to children in the form of foams and colloid suspensions.

Liquid preparations may be prepared from the powdered gentian root by treating about 20 grams of powdered gentian root with up to 100 ml of water and heating the mixture to a boil and then cooling the mixture to room temperature.

This should provide a solution having at least 20% by volume of active gentian root ingredient. Capsules may also be prepared and utilized for the treatment of systemic candidiasis and Cryptoccus. Capsules are prepared by utilizing the cleaned, heat treated and powdered gentian root in formulations having at least 20% by volume of active gentian root ingredient. The active gentian root ingredient can then be formulated with sweeteners other than sugar, flavorings or other excipients or carriers as are known to those skilled in the art. The resulting formulation with the gentian root active ingredient can be formulated in tablets or in gelatin, capsules and administered orally for the treatment of systemic candidiasis. The gentian root active ingredient may also be formulated with equal parts of American Radix Ginseng, Radix Scutellariae Basica Lensis and Fructus Gardeniae Jasminoidis for the treatment of *Cryptococcal meningitis* in AIDS patients or other patients with immuno-compromised immune systems.

The method and novel pharmaceutical preparations utilizing gentian root can be utilized to treat Candida and yeast infections of the vaginal tract. The novel preparations are effective in the treatment of candidiasis within 2 to 5 days utilizing creams, douches and preferably suppositories containing gentian root as the active ingredient. Creams and suppositories should contain at least 20% by volume of the gentian root active ingredient. Douches and solutions containing gentian root as an active ingredient should contain at least 20% by volume of the gentian root active ingredient. The douches and solutions are prepared as heretofore described.

Suppositories are prepared from gentian roots which are washed and dried. The gentian root is heated at low heat at about 100° F. for about 1½ hours to dry it without burning. The root is then ground to make a fine powder and sifted in a fine mesh sifter to collect the fine powder. The coarse part is discarded. A suppository base made of hydrogenated vegetable oil and glycol distearate ester and known as natural base as may be obtained from Professional Arts Pharmacy in Baltimore, Md. is heated in an oven until it gets soft. Once the suppository base is soft, it is cooled to 100° F. and mixed with the gentian powder in a ratio of 0.5 grams powder to 2.5 grams of the base. Thereafter the base material containing the gentian root active ingredient is filled into a suppository shell and kept at room temperature until the suppository solidifies which is then wrapped and provided to the patient. The suppositories are generally utilized by a patient for two to five days to control yeast and Candida infections of the vagina.

For systemic infection of Candida as well as the treatment of Cryptoccus, formulations including gentian root as the active ingredient may be utilized in the form of liquids, powders, tablets, capsules or foams for ingestion. These liquids, powders, foams or capsules are then taken orally on a daily basis until the cryptococcal infection or systemic candidiasis infection is brought under control. In the case of patients with AIDS or other immuno-suppressed patients such treatment can be taken continually in a form of a maintenance or suppression therapy. In the normally immune patient the A gentian formulations are taken for a period of 1 to 5 days to bring candidiasis mucosal infections under control and utilized for a period of about 10 days to bring systemic candidiasis and Cryptococcal infections under control. The advantages of the invention will be illustrated in Examples and described in the following detailed description of the preferred embodiments.

DETAILED DESCRIPTION OF THE PREFERRED EMBODIMENTS

The present invention pertains to the treatment of fungus and yeast infections with the use of pharmaceutical preparations containing gentian root or seeds which is administered orally in the case of systemic infections due to *Candida albicans* and *Cryptoccus neoformans* and which may be applied topically to infected mucosa or skin in the form of suppositories, lotions, foams, ointments and creams. Ordinarily Candida and Candida organisms, which have been referred to as *Candida albicans, Monilia albicans, Saccharomyces albicans, Odium albicans,* will be referred to here as Candida or *Candida albicans* live in a healthy balance with other bacteria and yeasts in the body. Candida normally inhabits the mouth, throat, intestine and genital tract. Certain conditions such as a depressed immune system, illness, obesity, diabetes and a variety of drugs including oral contraceptives and antibiotics can cause an infection known as candidiasis.

Vaginal yeast infections and fungus infections are caused by opportunistic organisms that in a balanced or healthy immune system are kept under control by the other natural flora and body defenses but which, when conditions are right, rapidly multiply, change phenotype and cause infection, such as in patients that have been treated with wide spectrum antibiotics, particularly tetracycline or have weak immune systems resulting from illness or compromised immune systems, such as AIDS. Because Candida can travel through the bloodstream it can infect many parts of the body and result in many different symptoms.

Candidiasis can infect various parts of the body, the most common being the ears, nose, gastrointestinal tract and bowels. The ability of *Candida albicans* to switch to at least seven different phenotypes defined by colony morphology which are also associated with changes in virulence make candidiasis difficult to detect and control. Treatment in immuno-suppressed patients presents particularly difficult problems particularly where systemic infection is involved. Symptoms of candidiasis can include constipation, diarrhea, colitis, abdominal pain, canker sores, persistent heartburn, muscle and joint pain, sore throat, congestion, nagging cough, numb hands, legs or face, tingling sensations, acne, vaginitis, kidney and bladder infections, arthritis, depression, hyperactivity, hypothyroidism followed by adrenal problems and even diabetes.

*Candida albicans* is generally kept in check in the vagina by complex interrelationship between the flora and body defense mechanisms which keep the pH in the range of 4.5 to 5. However, where *lactobacillus* and other beneficial fungus do not keep *Candida albicans* in check by maintaining pH in the range of 4.5 to 5 *Candida albicans* rapidly proliferates to cause infection. Vaginal and urinary tract yeast infections by *Candida albicans* are more likely to develop in pregnant or diabetic or women taking a contraceptive pill or having an iron deficiency. Candidiasis or yeast infections can occur in both male and female patients that have been taking broad spectrum antibiotics or corticoid medications which have disturbed the balance of the natural flora and result in fungus and yeast infections of the mouth or oral thrush and systemic infections resulting in the spread of the fungus throughout the body. The spread of yeast infections are particularly the problem in patients having weak immune systems or compromised immune systems such as AIDS or persons having leukemia or other disease which impair the body's ability to ward off such fungal attacks.

Cryptococcus similarly is a fungus or yeast infection caused by the yeast *Cryptoccus neoformans* which lives in soil and dried pigeon droppings. The disease results when a person inhales the organism which first resides in the lungs causing low grade fever, chest pain and a cough but which can spread from the lungs and infect the person systemically where the patient has a weak or compromised immune system. In many cases, where the patient does not havimmune system, the cryp immune system, the Cryptoccus is killed by the natural body defenses. In patients with weak or compromised immune systems, such as patients with leukemia, Hodgkin's disease or AIDS, the Cryptoccus infection can cause *Cryptoccus meningitis*. Cryptococcal infection in AIDS patients is particularly difficult to treat and has been particularly virulent. Amphotericin B is the traditional treatment for *Cryptoccus meningitis* in AIDS patients which has reduced mortality from Cryptococcal meningitis from 100% to 40%. However as previously indicated amphotericin B is toxic and in many cases is administered with flucytosine (5-fluorocytosine) for a period of 6 weeks followed by maintenance therapy with fluconazole, ketoconazole or amphotericin B.

In accordance with the invention the opportunistic infections caused by the fungus in yeast forms of *Candida albicans* and Cryptoccus are treated systemically and specifically in various organs of the body by pharmaceutical preparations prepared from gentian root which is administered topically or orally to an infected patient. The novel pharmaceutical preparations can be administered in the form of suppositories, lotions, creams, liquids, foams, capsules and tablets which include as their active ingredient preparations made from *Radix gentianae* Longdancao. Pharmaceutical preparations made in accordance with the invention are prepared from the root or seeds of *Radix gentianae* Longdancao, preferably obtained from China.

The gentian obtained from the gentian plant from China is known in Chinese as Longdancao and has been referred to in Chinese literature by its pharmaceutical name *Radix gentianae* Longdancao. The botanical name of *Radix gentianae* Longdancao has been referred to as *Gentiana scabra* Bge, *Gentiana triflora* Pall, *Gentiana manshurica* Kitag, *Gentiana algida* Pall, *Gentiana regescens* Fransh and *Gentiana lutea*. *Gentiana scabra* Bge and *Gentiana algida* Pall are grown throughout China, but especially in the northeast, whereas, *Gentiana triflora* Pall is grown in northeastern China and inner Mongolia, and *Gentiana manshurica* Kitag is grown in northeastern and eastern China. The roots and root stems of all of these varieties of gentian are useful for making pharmaceutical preparations in accordance with the invention. In addition, it is believed the European variety of gentian, namely *Gentiana lutea* is also effective in treating fungal infections caused by *Candida albicans* and *Cryptoccus neoformans* in accordance with the invention.

Gentian and gentian root is the active ingredient responsible for the pharmacological action against Candida and Cryptoccus. It is known that gentian and gentian root include a number of chemical constituents, including gentiopicrin (gentiopicroside) $C_{16}H_{20}O_9$, gentianine $C_{10}H_9NO_2$, gentianose $C_{18}H_{32}O_{16}$, gentisin $C_{14}H_{10}O_5$, gentisic acid $C_7H_6O_4$, gentibiose $C_{12}H_{22}O_{11}$, as well as gentiamarin $C_{16}H_{22}O_{10}$ or $C_{16}H_{20}O_{10}$, gentiin $C_{25}H_{23}O_{14}$, pectins, acids, including methyl fomannoxin acid and methyl anofinic acid, several alkaloids, gentialutine, yellow xanthone pigments, isogentisin and its glycoside gentioside triterpenes and sugars.

Pharmaceutical preparations of the invention made from whole gentian root *Radix gentianae* Longdancao by washing the gentian root, heating it for about 1 to 2 hours at from about 100 to 200° F. and grinding it into a fine powder which is then mixed with water to prepare solutions of gentian root or mixed with suitable carriers and excipients to create lotions, creams, foams or suppositories. For the preparation of lotions and liquids, powdered gentian root is added in the amount of 20 grams of powdered root per 100 ml of water to provide a mouthwash for the treatment of oral yeast infections. The mouthwash is taken 2 times a day and is used for the treatment of oral thrush or oropharyngeal moniliasis to bring oral thrush under control within 2 to 4 days after application.

Gentian suppositories may be made for the treatment of a vaginal yeast infection by first washing *Radix gentianae* Longdancao with water to remove all dust residues and thereafter heating the gentian roots in an oven at low temperature about 100 degrees Fahrenheit for about 1½ hours to dry and prepare the root without burning it. Thereafter, a grinder is utilized to make a fine powder from the cleaned, heat-treated, dried roots. The resulting product is then sifted through a flour sifter having a mesh of about 576 holes/cm² utilized to separate the fine powder from the coarse powder. The coarse part is discarded and the fine powder is used as the active ingredient for suppositories or creams. Creams may be prepared by utilizing such excipients and carriers as benzyl,alcohol, cetearyl alcohol, cetyl esters wax, octyldocticanol, polysorbate 60, sorbitan monostearate and other well-known pharmaceutical carriers.

To prepare suppositories the gentian active ingredient is prepared as previously discussed and the suppository base is heated until it gets soft and then it is cooled to about 100° F. at which time the active powder ingredient is mixed with the suppository base in accordance with the ratio of 0.5 grams of powder to 2.5 grams suppository base. Thereafter, the mixture is filled into a suppository shell of about 4.2 cm long, and about 0.7–1.1 cm in diameter (small end and large end, respectively) and is kept at room temperature until the suppository solidifies. The suppository weighs about 2.8 grams. Once the suppository has solidified, the suppositories are then packaged into an inert packaging medium until used.

The suppositories are then utilized by the patient having a Candida infection. The treatment of candidiasis in mucosal tissue and particularly the vagina can be treated effectively with gentian suppositories or with gentian douches, creams or ointments with the gentian suppository being in accordance with the best mode of the invention. The gentian suppositories and liquids prepared in accordance with the invention were tested in vivo which provides the most reliable results since in vivo tests provide actual clinical response and demonstrate the effectiveness of the drug and its delivery to the infection site under actual conditions in relation to the particular phenotype of Candida causing the infection as well as the actual status of the patient's heredity, immune status, nutritional and health condition.

The invention has been the result of an extensive research investigation into opportunistic fungal infections caused by changes in the colonization flora of the human body as it interplays with nutrition, genetics, and impaired immunity and the complex factors which are normally responsible for the prevention of fungal outbreaks of *Candida albicans* and *Cryptoccus neoformans*. The present investigations have focused upon in vivo studies since in vitro studies are highly unpredictable in terms of efficacy of drugs. In vitro studies do not account for tissue absorption and permeability, genetics, changes in body pH and the interplay between body function conditions and fungal and yeast phenotype. These conditions cannot be replicated in in vitro studies, and have resulted in poor correlation between in vitro studies and eventual in vivo applications. The extensive research investigations have included patients with,impaired and suppressed immune systems, as well as a complex interrelation between nutrition, health, history of antibiotic use and the different phenotypes of the fungal colonies in relation to the health of the individual in the following Examples. These studies have confirmed the efficacy, lack of toxicity, and reliability of the pharmaceutical preparations of the present invention which include gentian as the active ingredient.

The in vivo Examples demonstrate the effectiveness of the method of treatment and pharmaceutical preparations using *Radix gentianae* Longdancao as an active ingredient for the treatment of mucosal and systemic candidiasis and *Cryptoccus mycosis*. The method of treatment and in vivo tests in immuno-compromised patients and patients having systemic candidiasis are particularly significant since mycosis was controlled despite the condition of the immune system and the particular phenotype or virulence of the colony morphology in relation to the balance of the other bacterial flora. The utilization of the invention for the treatment of candidiasis of mucosal membranes is illustrated by the following Examples 2 to 15 and 17, Examples 17 to 25 and Example 27.

EXAMPLE 1

In this Example suppositories were prepared for the transmucosal treatment of vaginal yeast infection by washing gentian roots with water and thereafter heating the roots to 100° F. without burning the roots for about 1½ hours to prepare the roots. Thereafter the heat treated roots were ground in a grinder to make a fine powder. The fine powder was sifted in a flour sifter having a mesh about 576 holes/cm$^2$ and the coarse part was discarded with the powder saved as the active ingredient for the suppository. A suppository base was then heated until it was soft and cooled to 100° F. before mixing the gentian powder active ingredient with the base in a ratio of 0.5 grams of powder to 2.5 grams of base to prepare suppositories of about 2.8 grams and of a size of about 4.2 centimeters long and 0.7–1.1 centimeters in diameter (small end and large end respectively). These suppositories were then administered to patients in the following Examples 2–15 and 17.

EXAMPLE 2

In this Example one suppository prepared in accordance with Example 1 was administered daily to a patient suffering from vaginal yeast infection. The patient was female and 66 years old and had been previously treated with antibiotics. The suppositories were administered over a 5-day period. The patient was cured of the vaginal yeast infection after a 5-day period of treatment.

EXAMPLE 3

In this Example one suppository prepared in accordance with Example 1 was administered daily to a patient suffering from vaginal yeast infection. The patient was female and 37 years old and had suffered from an ear infection and had been previously using antibiotics. The patient was cured of the vaginal yeast infection after a 3-day period of treatment.

EXAMPLE 4

In this Example one suppository prepared in accordance with Example 1 was administered daily to a patient suffering from vaginal yeast infection. The patient was female and 45 years old and felt weak. The patient was cured of the vaginal yeast infection after a 3-day period of treatment. After 1–2 hours after using the suppository the patient reported that she felt better.

EXAMPLE 5

In this Example one suppository prepared in accordance with Example 1 was administered daily to a patient suffering from vaginal yeast infection. The patient was female and 36 years old and reported being under stress and felt weak. The patient was cured of the vaginal yeast infection after a 2-day period of treatment.

EXAMPLE 6

In this Example one suppository prepared in accordance with Example 1 was administered daily to a patient suffering from vaginal yeast infection. The patient was female and 52 years old and suffering from urinary tract infection which had previously been treated with antibiotics. The patient was cured of the vaginal yeast infection after a 3-day period of treatment. The patient reported relief 1½ hours after using the suppository.

EXAMPLE 7

In this Example one suppository prepared in accordance with Example 1 was administered daily to a patient suffering from vaginal yeast infection. The patient was female and 34 years old, felt weak and suffered from endometriosis and interstitial cystitis, was weak and had previously been using antibiotics. The patient was cured of the vaginal yeast infection after a 3-day period of treatment, The patient reported that she felt better within 2–3 hours after using the suppository.

EXAMPLE 8

In this Example one suppository prepared in accordance with Example 1 was administered daily to a patient suffering from vaginal yeast infection. The patient was female and 45 years old and felt weak. The patient was cured of the vaginal yeast infection after a 3-day period of treatment.

EXAMPLE 9

In this Example one suppository prepared in accordance with Example 1 was administered daily to a patient suffering from vaginal yeast infection. The patient was female and 52 years old and suffered from urinary tract infection and had previously been treated with antibiotics. The patient was cured of the vaginal yeast infection and after about 1½ hours the symptoms were controlled.

EXAMPLE 10

In this Example one suppository prepared in accordance with Example 1 was administered daily to a patient suffering from vaginal yeast infection. The patient was female and 34 years old and suffered from endometriosis and interstitial cystitis. The patient was cured of the vaginal yeast infection after a 3-day period of treatment.

EXAMPLE 11

In this Example one suppository prepared in accordance with Example 1 was administered daily to a patient suffering from vaginal yeast infection. The patient was female and 37 years old and also suffered from an ear infection and had previously been using antibiotics. The patient was cured of the vaginal yeast infection after a 3-day period of treatment.

EXAMPLE 12

In this Example one suppository prepared in accordance with Example 1 was administered daily to a patient suffering from vaginal yeast infection. The patient was female and 36 years old and suffered from stress and reported being weak. The patient was cured of the vaginal yeast infection after a 2-day period of treatment.

EXAMPLE 13

In this Example one suppository prepared in accordance with Example 1 was administered daily to a patient suffering from vaginal yeast infection. The patient was female and 34 years old and suffered from stress. The patient was cured of the vaginal yeast infection after a 2-day period of treatment.

EXAMPLE 14

In this Example one suppository prepared in accordance with Example 1 was administered daily to a patient suffering from vaginal yeast infection. The patient was female and 65 years old and also reported suffering from weakness. The patient was cured of the vaginal yeast infection and the vaginal discharge was stopped within 3 hours of treatment with the novel suppository of the invention.

EXAMPLE 15

In this Example one suppository prepared in accordance with Example 1 was administered daily to a patient suffering from vaginal yeast infection. The patient was female and 40 years old and tended to overeat sweets. The patient was cured of the vaginal yeast infection after a 2-day period of treatment.

EXAMPLE 16

In this Example, a solution for the treatment of candidiasis was prepared by first washing in water the gentian root from the plant *Gentiana algida* Pall obtained from China to remove dirt and dust. The gentian root is heated in an oven at 100° F. for about 1½ hours and removed and cooled before it is ground to make a fine powder in a 9092 Fine Herb Grinder. The powder is sifted through a copper sieve for white flour having a mesh of about 576/cm². 20 grams of powder passing through the sieve is placed in a 100 ml beaker which is filled with water to the 100 ml mark and the entire contents is placed into a ceramic pot and the mixture is brought to a boil and then allowed to simmer for 20 minutes. The resulting first liquid is strained into a container and saved.

The remaining strained root is placed back into the ceramic pot and a second portion of 100 ml of water is added and the mixture is brought to a boil and again simmered for 20 minutes. The resulting liquid is strained and mixed with the resulting first liquid to provide a total of about 200 ml of solution having gentian root as an active ingredient.

EXAMPLE 17

In this Example one suppository prepared in accordance with Example 1 was administered daily to a patient suffering from vaginal yeast infection. In addition 200 ml of the solution prepared in accordance with Example 1 ≠was administered daily to treat systemic candidiasis. The patient was female and 56 years old and suffered from both a vaginal yeast infection and systemic candidiasis. The patient was cured of both systemic candidiasis and the vaginal yeast infection after a 2-day period of treatment. The patient reported that she felt better after about 1–2 hours after using the suppository.

EXAMPLE 18

In this Example 200 ml of the solution prepared in accordance with Example 16 was administered daily to a patient suffering from oral thrush. The patient was male and 36 years old and was suffering from HIV. The solution was both ingested and used as a mouth wash over a 3-day period. The patient was cured of oral thrush in the 3-day period.

EXAMPLE 19

In this Example 200 ml of the solution prepared in accordance with Example 16 was administered daily to a patient suffering from oral yeast infection. The patient was female and 64 years old and was suffering from throat cancer and the consequences of radiation received to treat throat cancer. The solution was both ingested and used as a mouth wash. In a 2-day period after the start of the treatment the oral yeast infection disappeared.

EXAMPLE 20

In this Example 200 ml of the solution prepared in accordance with Example 16 was administered daily to a patient suffering from oral yeast infection and systemic candidiasis. The patient was female and 5 years old. The solution was both ingested and used as a mouth wash over a 3-day period. The patient was cured of the oral yeast infection and systemic candidiasis in a 3-day period.

EXAMPLE 21

In this Example 200 ml of the solution prepared in accordance with Example 16 was administered daily to a patient suffering from oral yeast infection. The patient was male and 21 years old and was suffering from a brain tumor and was using hydrocortisone. The solution was both ingested and used as a mouth wash over the entire period of treatment. The patient was cured of the oral yeast infection in a 4–5 day period.

EXAMPLE 22

In this Example 200 ml of the solution prepared in accordance with Example 16 was administered daily to a patient suffering from oral yeast infection. The patient was male and 32 years old and was suffering from HIV. The solution was both ingested and used as a mouth wash over the entire period of treatment. The patient was cured of the oral yeast infection in a 3-day period.

EXAMPLE 23

In this Example 200 ml of the solution prepared in accordance with Example 16 was administered daily to a patient suffering from oral yeast infection. The patient was male and 35 years old and was suffering from HIV. The solution was both ingested and used as a mouth wash over the entire period of treatment. The patient was cured of the oral yeast infection in a 4–5 day period.

EXAMPLE 24

In this Example 200 ml of the solution prepared in accordance with Example 16 was administered as a douche daily to a patient suffering from a vaginal yeast infection. The patient was female and 66 years old and was suffering from frequent urinary tract infections who had been previously treated with antibiotics. The patient was cured of the vaginal yeast infection after a 2-day period of treatment.

EXAMPLE 25

In this Example 200 ml of the solution prepared in accordance with Example 16 was administered as a douche daily to a patient suffering from a vaginal yeast infection. The patient was female and 48 years old and felt weak. The patient was cured of the vaginal yeast infection after a 2-day period of treatment.

EXAMPLE 26

In this example a liquid pharmaceutical preparation for the treatment of Cryptoccus meningitis caused by the fungus Cryptoccus was prepared by first washing in water gentian root from the plant *Gentiana algida* Pall obtained from China to remove dust. The gentian root was then heated in an oven at 100° F. for about 1½ hours. The cooled root was then ground into a fine powder which was sifted through a copper sieve having a mesh of about 576 holes/cm$^2$.

3 grams of the fine powder was mixed with 3 grams of powdered American Radix Ginseng, 3 grams of powdered Radix Scutellariae Basica Lensis and 3 grams of Fructus Gardeniae Jasminoidis. The resulting 9 gram mixture was then added to about 100 ml of water and brought to a boil and then allowed to simmer for about 20 minutes. The mixture was then cooled and strained to remove large particulate matter to provide a liquid pharmaceutical preparation.

EXAMPLE 27

In this Example the pharmaceutical preparation made in accordance with Example 26 was utilized to treat an AIDS patient with Cryptoccus meningitis caused by the fungus Cryptoccus. This patient was about 40 years of age, was too weak to walk, had a headache, nausea, vomiting and stiff neck. At the time of the patient's visit the patient was driven to the office by a chauffeur and visited the office for approximately ten minutes at which time a preparation in accordance with the Example 26 was administered once a day for of a period of three days at which time the patient returned to the office without assistance. The pharmaceutical preparation was administered to the patient for another three day period.

Later the patient was followed-up at a meeting in San Francisco about one month later and was found to have been cured of Cryptoccus meningitis. The gentian root taken in the preparation administered orally appears to have entered the blood stream and penetrated the blood-brain barrier to get into the cerebral spinal fluid to kill the Cryptoccus fungus.

The foregoing Examples and method of treatment of fungal infections with pharmaceutical preparations containing gentian root as the active ingredient demonstrate the efficacy of the invention in vivo. The foregoing in vivo Examples also illustrate oral administration of the novel pharmaceutical preparations containing gentian root as the active ingredient is able to enter the bloodstream to cure systemic candidiasis and is able to pass through the blood brain barrier to cure Cryptococcal meningitis. In the case of Cryptococcal meningitis additional active ingredients such as American Radix Ginseng, Radix Scutellariae Basica Lensis and Fructus Gardeniae Jasminoidis may be added to the preparation.

It is further contemplated that pharmaceutical preparations from the active ingredients in gentian root can be administered by IV or parenterally by subcutaneous injection to cure systemic candidiasis when required for incapacitated patients. It is also contemplated that pharmaceutical preparations for the treatment of mucosal infections can be administered by administering an effective amount of the pharmaceutical preparations of the invention. The novel pharmaceutical preparations may be administered orally or transmucosally in the form of lotions, creams, foams, suppositories and solutions. The novel preparations of the invention may be formulated as suppositories, mouth washes, creams, lotions and troches utilizing a variety of fillers, flavorings, artificial sweeteners but not sugar and other excipients as are well known to those skilled in the art.

The treatment of candidiasis in accordance with the invention results in a cure in 2 to 3 days with patients having a normal immune system and 3 days to a week in patients having a weak or compromised immune system. In cases of vaginal yeast infections suppositories constructed in accordance with the invention generally bring vaginal yeast infections under control within 1 to 5 days of treatment. Maintenance or suppression therapy may be utilized in patients having a deficient or impaired immune system resulting from diseases such as leukemia, AIDS, Hodgkin's disease or other neutropenic conditions. Maintenance or suppression therapy may also be utilized in patients taking tetracycline or other antibiotics to control Cryptoccus and candidiasis. Suppression therapy may be achieved by the administration of pharmaceuticals formed in accordance with the invention utilizing gentian root as an active ingredient together with carriers and other excipients as are customarily used by those skilled in the art.

Those skilled in the art will recognize the invention may be utilized and modified in a number of ways to provide for the control and regulation of *Candida albicans* and *Cryptoccus neoformans* in the human body in a variety of therapeutic applications. The pharmaceutical preparations of the present invention utilizing gentian root as an active ingredient may be utilized to not only treat and cure candidiasis and Cryptococcal meningitis infections, but also may be utilized for maintenance or suppression therapy to make certain that individuals with suppressed or deficient immune systems are assisted in the prevention of further yeast infections by *Candida albicans* and *Cryptoccus neoformans*. For example, maintenance or suppression therapy may be utilized prior to transplant operation or by the co-administration of gentian root with tetracycline or other wide spectrum antibiotics to prevent candidiasis.

As will be further recognized by those skilled in the art, the formulations of the invention may be implemented in a variety of ways to suit particular dosage requirements in view of age, immunological condition of the patient, as well as the severity of the fungal or yeast infection to suit particular requirements. These modifications to the formulations utilizing gentian root as an active ingredient may be made within the scope of the invention as defined in the following claims:

What is claimed is:

1. A method of treating a fungal infection caused by Cryptococcus comprising: administering a composition containing an effective amount of a therapeutic agent selected from the constituents of gentian in combination with a pharmaceutically acceptable carrier to a patient.

2. A method according to claim 1 wherein the composition comprises gentian.

3. The method according to claim 2 wherein said gentian is, obtained from *Radix gentianae* Longdancao.

4. The method according to claim 2 wherein gentian root is heated without burning at from about 100 to 200 ° F. and powdered before being combined with said pharmaceutically acceptable carrier.

5. The method of according to claim 1 wherein said composition is administered parenterally, transmucosally, topically, sublingually, intravaginally, orally or a combination thereof.

6. The method according to claim 1 wherein said pharmaceutically acceptable carrier is a gelatin capsule.

7. The method of treating fungal infection of claim 1 wherein said pharmaceutically acceptable carrier is a foam.

8. The method of treating fungal infection of claim 1 wherein said pharmaceutically acceptable carrier is water.

9. The method of treating fungal infection of claim 1 wherein said pharmaceutically acceptable carrier comprises a hydrogenated vegetable oil and a glycol distearate ester.

10. A method according to claim 1 wherein Cryptococcus is Cryptococcal meningitis.

11. A suppository for the treatment of vaginal yeast infection caused by *Candida albicans* comprising a composition containing an effective amount of a therapeutic agent selected from the constituents of gentian in combination with a pharmaceutically acceptable carrier.

12. The suppository according to claim 11 wherein the composition comprises gentian.

13. The suppository according to claim 12 wherein said gentian is obtained from *Radix gentianae* Longdancao.

14. The suppository according to claim 12 wherein said gentian is obtained from gentian seeds.

15. The suppository according to claim 12 wherein said gentian is obtained from the gentian plant.

16. The suppository according to claim 12 wherein said pharmaceutically acceptable carrier comprises a hydrogenated vegetable oil and a glycol distearate ester.

17. A method of treating a patient suffering from a vaginal yeast infection caused by *Candida albicans* comprising administering a suppository having the composition according to claim 12.

18. A method of treating a patient having a systemic fungal infection caused by *Candida albicans* or Cryptococcus comprising administering a composition comprising an effective amount of a therapeutic agent selected from the constituents of gentian in combination with a pharmaceutically acceptable carrier.

19. The method according to claim 18 wherein the composition comprises gentian.

20. A method of treating a mucosal infection including vaginal yeast infection caused by Candida or Crypyococcus comprising administering a composition comprising an effective amount of a therapeutic agent selected from the constituents of gentian in combination with a pharmaceutically acceptable carrier to a patient.

21. The method according to claim 20 wherein the composition comprises gentian.

* * * * *